United States Patent [19]

McAnalley et al.

[11] Patent Number: 4,846,170

[45] Date of Patent: Jul. 11, 1989

[54] GAS DELIVERY APPARATUS PROTECTION DEVICE

[76] Inventors: Bill H. McAnalley, 4602 Chalk Crt., Grand Prairie, Tex. 75052; Wiley F. Walker, 1709 Roman Rd., Grand Prairie, Tex. 75050

[21] Appl. No.: 161,219

[22] Filed: Feb. 17, 1988

Related U.S. Application Data

[63] Continuation of Ser. No. 932,784, Nov. 19, 1986, abandoned.

[51] Int. Cl.$^4$ .............................................. A62B 23/06
[52] U.S. Cl. ......................... 128/207.13; 128/207.18; 128/909
[58] Field of Search ...................... 128/205.25, 205.27, 128/205.28, 205.29, 206.11, 206.12, 206.16, 206.17, 206.18, 206.19, 206.21, 206.22, 206.28, 207.13, 207.18, 909, 910

[56] References Cited

U.S. PATENT DOCUMENTS 4,361,146 11/1982 Woicke ........................... 128/206.16

OTHER PUBLICATIONS

Milgrom, P. et al., "Local Anaesthetic Adverse Effects and Other Emergency Problems in General Dental Practice", International Dental Journal (1986) 36, 71-76.

Yagiela, J. A. et al., "Disinfection of Nitrous Oxide Inhalation Equipment", JADA, vol. 98, Feb. 1979, pp. 191-195.

Problems with Anesthetic and Respiratory Therapy Equipment, Rendell-Baker, L., ed. Little, Brown and Company 1982, vol. 20, No. 3 pp. 153-170.

Freeley, T. W., et al., "Sterile Anesthesia Breathing Circuits Do Not Prevent Postoperative Pulmonary Infection", Anesthesiology.
54: 369-372, 1981.

Nielsen, H., et al., "Cross-Infection From Contaminated Anaesthetic Equipment. A Real Hazard?", Anaesthesia, 1980, vol. 35, pp. 703-708.

Primary Examiner—Ruth S. Smith
Assistant Examiner—John P. Lacyk
Attorney, Agent, or Firm—Hubbard, Thurman, Turner & Tucker

[57] ABSTRACT

A gas delivery apparatus protection device that is used in combination with gas delivery systems. The gas delivery apparatus protection device is permeable to inhalation gases, but reduces the possibility of the transfer of undesirable agents from one user to another. These agents include pathogens, chemicals, cosmetics, drugs, viruses, bacteria and molds.

1 Claim, 1 Drawing Sheet

GAS DELIVERY APPARATUS PROTECTION DEVICE

This application is a continuation, of application Ser. No. 932,784, filed Nov. 19, 1986 now abandoned.

BACKGROUND OF THE INVENTION

1. Field of the Invention

The present invention relates to a new device which is effective in isolating gas delivery apparatus used in the dental office from a patient's skin and mucous membranes. The device is especially useful in preventing cross-contamination of patients from contaminated anesthetic equipment.

2. Description of the Prior Art

Increasing concern over the role of the dental profession in the transmission of infectious disease has focused attention on the proper sterilization of dental equipment. One instrument that has largely escaped consideration is the nitrous oxide gas machine with its attendant tubing, nasal hood, and reservoir bag. Recommendations for routine cleaning of nitrous oxide equipment vary from spraying the nasal hood with scented alcohol to washing all rubber goods with soap and water. It is questionable whether these or other techniques currently in general use provide adequate disinfection. Microbial cross-contamination during sedation with nitrous oxide has not been considered a major problem, but related inhalation devices have been linked with nosocomial infections.

Anesthetic and other inhalation devices are clearly sources for the iatrogenic transmission of infectious disease. Microorganisms have been recovered from virtually every portion of the anesthetic breathing circuit. The microorganisms that have been isolated from anesthetic and inhalation equipment include known pathogens, such as *Candida albicans, Clostridium perfringens, Escherichia coli, Haemophilus influenzae suis, Klebsiella pneumoniae, Mycobacterium tuberculosis, Pseudomonas aeruginosa, Salmonella montivedeo, Staphylococcus aureus, Streptococcus pyogenes,* and the *Viridans streptococci*. It can be assumed that various mycoplasma, viruses, and other organisms not evaluated may also be present in the anesthetic devices.

Accordingly, the possibility exists that dental practitioners using nonsterile equipment may be facilitating the spread of infectious disease. This possibility was examined by Yagiela et al., JADA, Vol. 98, February 1979, pp. 191–195, who administered nitrous oxide and oxygen to patients for 30 minutes. In nine of 21 instances, bacteria morphologically identical with organisms isolated from the nasal mucosa of the patients were cultivated from the used nasal hoods. Further experiments with an artificial breathing system designed to mimic human respiration showed that bacteria deposited on nasal hoods were routinely dislodged and inspired during subsequent use.

Yagiela et al. concluded that traditional cleaning methods involving soap and water rinses, alcohol sprays or swabs, or commercial cleaners may provide some degree of disinfection, but they cannot be relied on to produce total sterility. Yagiela et al. propounded that more effective techniques are generally impractical. Tubing and nasal hoods are easily damaged by high temperatures in an autoclave, and monetary and space requirements for sterilization with ethylene oxide are prohibitive. They proposed that perhaps the best compromise between effectiveness and practicality is to disinfect with a "cold" germicidal solution and identified alkaline glutaraldehyde as the most suitable preparation available. They observed that glutaraldehyde does not coagulate proteins, and it remains active in the presence of mucus and blood. Deterioration of rubber and plastic is not an important problem. Because of its low surface tension, glutaraldehyde penetrates small spaces easily and is readily removed by rinsing with water. Finally, alkaline glutaraldehyde is the most effective germicide in use; a ten-minute submersion at room temperature is sufficient to kill all microorganisms, with the exception of spores, which may require as long as ten hours of submersion.

More recently, and as discussed by Milgrom et al., International Dental Journal (1986) 36, 71–76, both AIDS and hepatitis have caused considerable stress and worry to general practitioners and specialists in urban areas throughout the world. The recognition of the hazard is paramount if appropriate precautions to protect dental office personnel are to be taken.

Because so little is known about the spread of AIDS and because carriers remain unidentifiable to the dentist, precautions must be taken. It is believed that the causative agent is a virus. Control measures to prevent contact with saliva and blood are appropriate in higher risk individuals. Surgical gloves or doubled examination gloves are required for all procedures. Glasses, masks and gown should be worn if aerosolization or splatter will take place. All contaminated material should be sterilized and disposed of properly. All instruments including hand pieces should be heat sterilized although glutaraldehyde products appear to be an acceptable substitute when heat sterilization is impossible.

Currently many different gas apparatus are used to deliver gas to people and animals. For example, nitrous oxide or laughing gas is used in dental offices and delivered to patients through a device called a hood that covers a patient's nose. The dental hood fits close to the face to reduce gas escaping into the dental office. Most of these hoods are subjected to time consuming cleaning and are reused. As discussed above, chemicals such as glutaraldehyde are usually used to disinfect the mask and to remove cosmetics, drugs, viruses, bacteria, mold and other unwanted materials, so these agents are not transferred to the next patient. In this regard, it is important to note that aldehydes have been implicated as having carcinogenic activity.

In the last few years small vacuum or scavenging systems have been added to dental hoods to aid in the removal of nitrous oxide that escapes from old style hoods. The addition of these systems has made cleaning harder, more time consuming, and in some cases, almost impossible. In many cases more cleaning time means more contact time of cleaning chemicals that may accelerate the deterioration of the gas hood. With this problem and the development of knowledge of the existence of the AIDS virus and other agents that could be transferred from patient to patient, a need was recognized for a disposable material to fill the gap between the gas delivery appartus and the patient. This disposable material should allow free gas exchange but reduce direct contact between the apparatus and the patient.

SUMMARY OF THE INVENTION

The device for protecting gas delivery apparatus of the present invention avoids the above-mentioned disadvantages and drawbacks which are characteristic of the prior art. The device of the present invention provides a means for isolating gas delivery apparatus used in the dental office from a patient's skin and mucous membranes. The device for protecting gas delivery apparatus of the present invention reduces the possibility of patient exposure to pathogens from delivery devices used to administer inhalation gases and consequently reduces the possibility of contamination of masks, hoods, and tubing used to administer inhalation gases.

The device for protecting gas delivery apparatus of the present invention comprises disposable sterile liner means adapted to be received in gas hood means, which disposable liner means is permeable to inhalation gases. Those skilled in the art will recognize that the degree of permeability to inhalation gases will vary with the thickness and pore shape of the material used. Preferably, the device of the present invention is adapted to be received in a close-fitting nestable arrangement with gas hood means such as conventional dental gas hoods and oxygen masks.

The device of the present invention, preferably, may be made of any material that meets the following material criteria (CM):

(1) CM is preferably a material considered safe for human contact, and for humans to breathe through.

(2) CM is preferably a material that is permeable to inhalation gases and allows sufficient air flow to enable a patient using the device to breathe normally.

(3) CM is preferably a material that is inert to the anesthetic gas or gas mixture being delivered to the patient.

(4) CM is preferably a material that can be molded by itself or in combination with glues, binders, adhesives or fixatives to be close fitting in a nestable arrangement with gas hoods, such as conventional dental gas hoods, oxygen masks and other human gas delivery devices.

(5) CM is preferably capable of being made in a sterile form or capable of being sterilized by dry heat, wet heat, chemicals or by gamma irradiation.

(6) CM preferably has a shelf life of at least one year.

The device of the present invention isolates the gas hood means from the patient's skin. As a consequence the hood is easier to clean as cosmetics and other materials are not transferred from the patient's skin to the gas hood. Moreover, the possibility of cross-contamination by transfer of pathogens, chemicals, cosmetics, drugs, viruses, bacteria and molds is reduced.

BRIEF DESCRIPTION OF THE DRAWINGS

In describing the invention, reference will be made to the accompanying drawings in which.

DETAILED DESCRIPTION OF THE PREFERRED EMBODIMENTS

Figure 2:
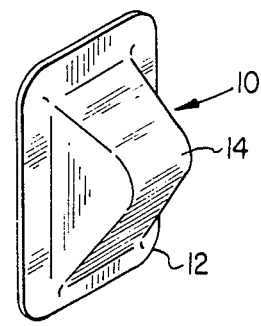
FIG. 2 is a perspective view of the gas delivery apparatus protection device of the present invention in isolation.

Referring now to the drawings, and in particular FIG. 2, a gas delivery protection device generally indicated at 10 is made of a material that is permeable to inhalation gases and allows sufficient air flow to enable a patient fitted with the device to breathe normally. Also, the material of the device is, preferably, inert to inhalation gases and is nonallergenic. Moreover, the material is, preferably, capable of being made in a sterile form by well-known conventional techniques or capable of being sterilized by well-known conventional techniques of dry heat, wet heat, chemicals or by gamma irradiation. Finally, the material, preferably, has a shelf life of at least one year.

Figure 1:
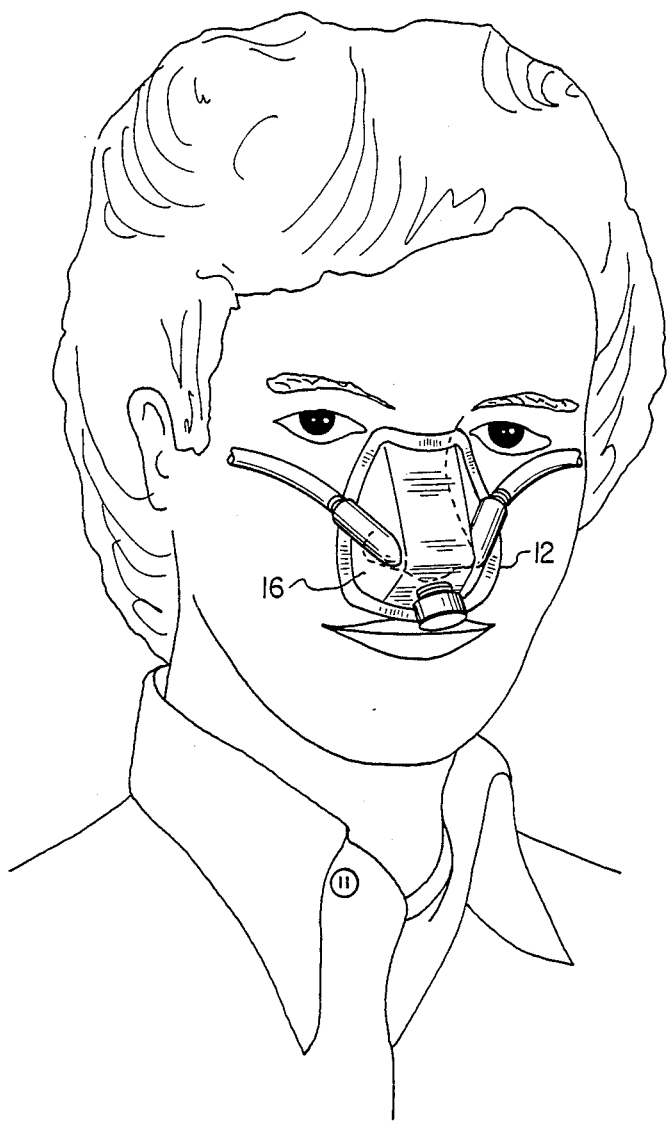
FIG. 1 is a perspective view of the gas delivery apparatus protection device of the present invention, a conventional gas hood and a patient.
Figure 3:
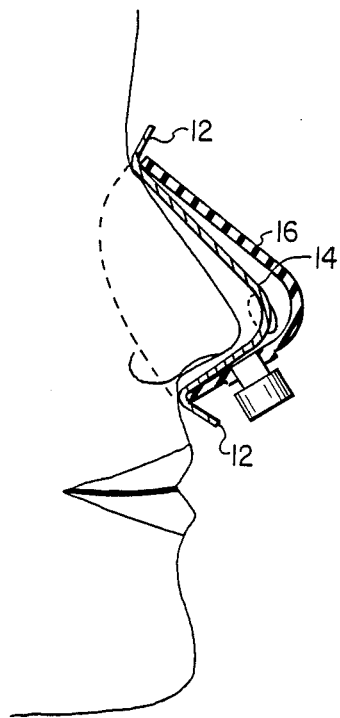
FIG. 3 is a section of the gas delivery apparatus protection device of the present invention and a conventional gas hood covering a patient's nose.

The material of the device must also be suitable for molding alone or in combination with glues, binders, adhesives, or fixatives. The gas delivery protection device 10, as shown in FIGS. 1 and 3 may be molded to be close fitting in a nestable arrangement with any conventional gas hood 16. Representative conventional gas hoods are made by Ohmeda (8420 South Continental Divide Road, Littleton, CO 80127), Porter Instrument Co. (P.O. Box 326, Hatfield, PA 19440), M.D.P. Diagnostic Co. (P.O. Box 10688, North Charleston, S.C. 29411) and Mission Dental (1017 West 5th Street North, Summerville, S.C. 29483).

As shown in FIG. 2, a gas delivery apparatus protection device 10 of the present invention includes a base portion 12 and a nasal projection portion 14. As shown in FIGS. 1 and 3, in use the base portion 12 is in contact with the patient's skin and prevents any part of a conventional hood 16 from contacting the patient's skin. As shown in FIG. 3, in use the nasal projection portion 14 accomodates the patient's nose and is large enough to provide clearance therebetween. It will be apparent to those skilled in the art that the base portion 12 of the gas delivery apparatus protection device 10 may be fabricated so the device cooperates with a specific conventional gas hood 16 or so the device cooperates with any conventional gas hood 16 while preventing the hood 16 from contacting the patient's skin. It will also be apparent that the device 10 of the present invention may be fabricated in different sizes to be useful in infant, child and adult applications.

As mentioned above, the base portion 12 of the device 10 is in contact with the patient's skin and prevents any part of a conventional hood 16 from contacting the patient's skin. As a consequence, the conventional hood 16 is easier to clean after patient use since cosmetics and other materials are not transferred from the patient's skin to the hood 16. Moreover, the device 10 acts in much the same manner as a surgical mask to trap and prevent the transferrance of a certain percentage of airborne pathogens, chemicals, viruses, bacteria and molds. Thus, the possibility of cross-contamination of patients by transfer of pathogens, chemicals, cosmetics, drugs, viruses, bacteria and molds is reduced. Preferably, the possibility of cross-contamination of patients by transfer of AIDS, herpes or hepatitis is reduced.

Figure 4:
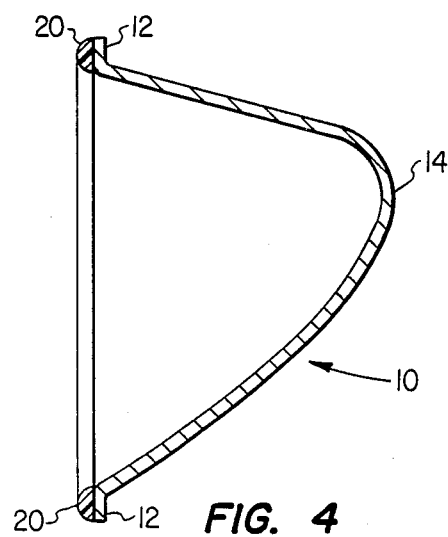
FIG. 4 is a section of a preferred gas delivery protection device of the present invention.

In a preferred embodiment shown in FIG. 4, a peripheral annular ring 20 of a substance such as silicone or latex rubber may be attached to the base portion 12 of the gas delivery protection device 10 of the present invention to provide more comfort to the patient at the skin contacting portion of the device.

A suitable and preferred material for the gas delivery apparatus protection device 10 of the present invention is spunbonded polyester. An especially suitable spunbonded polyester is sold under the trade name REEMAY ™ and is available from E.I. du Pont de Nemours & Co. (Inc.), Wilmington, Del., 19898. REE- MAY ™ is available as a sheet structure of continuous filament polyester fibers that are randomly arranged, highly dispersed, and bonded at the filament junctions.

REEMAY ™ is available in three basic product styles which use straight 4 denier per filament (dpf) (4.4 dtex) fibers, straight 2.2 dpf (2.4 dtex) fibers, or crimped 4 dpf (4.4 dtex) fibers. Average physical properties of REEMAY ™ reported by du Pont are found in Table I. These fibers give the various product styles different tactile, visual, and functional qualities. The crimped fibers give a soft, conformable hand while the straight fibers give a firmer and crisper hand.

For purposes of the present invention the 2.2 dpf straight fibers are preferred and fibers according to style number 2295 are most preferred.

REEMAY ™ spunbonded polyester combines the chemical and thermal properties of polyester fibers with the spunbonded structure to give it many outstanding features. These include: high tensile strength; high elongation to break; excellent tear strength; diverse range of bulk, porosity, and unit weight; good dimensional stability wet or dry; non-raveling edges; nondusting; high resistance to chemicals; not affected by water, rot, or mildew; resistant to temperatures up to 400° F. (205° C.) under normal conditions; and non-irritating to the skin.

REEMAY ™ is especially suitable for molding because it has: excellent mold conformability, especially the crimped styles; excellent molded shape retention; high tensile and tear strength; low substrate pattern strike-through; and high dielectric bond strength.

Another suitable and preferred material for the gas delivery apparatus protection device 10 of the present invention is randomly dispersed, continuous, high-strength polypropylene fibers. An especially suitable randomly dispersed continuous, high-strength polypropylene fiber product is sold under the trade name Cyclean ™ Filter Media and is available from Kimberly-Clark Corporation, Filtration Products Group, Nonwoven Fabrics Division, 1400 Holcomb Bridge Road, Roswell, Ga. 30076. Average physical properties of Cyclean ™ Filter Media reported by Kimberly-Clark are found in Table II.

TABLE II

AVERAGE PHYSICAL PROPERTIES OF CYCLEAN ™ FILTER MEDIA

| Product Description | Basis Weight (oz/yd$^2$) | Grab Tensile lbs. (MD/CD) | Trapezoidal Tear lbs. (MD/CD) | Mullen Burst (psi) | Frazier Perm. (CFM/Ft$^2$) | Thickness (Inches) |
|---|---|---|---|---|---|---|
| HP40 | 0.40 | 6/7 | 2.5/2.8 | 15 | 680 | 0.006 |
| HP80 | 0.80 | 10/13 | 2.2/3.4 | 24 | 453 | 0.009 |
| HP100 | 1.00 | 17/20 | 4.8/5.5 | 29 | 362 | 0.011 |
| HP125 | 1.25 | 23/23 | 4.9/5.9 | 37 | 247 | 0.012 |
| HP150 | 1.50 | 25/28 | 4.9/7.4 | 41 | 198 | 0.015 |
| HP200 | 2.00 | 32/39 | 7.9/8.8 | 47 | 142 | 0.017 |
| HP250 | 2.50 | 42/47 | 10.0/10.0 | 71 | 96 | 0.024 |

Another suitable and preferred material for the gas delivery apparatus protection device 10 of the present invention is cellulose-acetate. Those skilled in the art will be aware of suitable cellulose-acetate materials that may be used for the gas delivery apparatus protection device 10 of the present invention.

A manufacturing process for the gas delivery apparatus protection device of the present invention utilizing a spunbonded fabric or a melt blown fabric is described below. Spunbonded fabric is a "nonwoven" fabric manufactured by extruding resins (polyester, polypropylene, etc.) through dies or spinnerets to form continuous fibers. These continuous filaments are laid on an apron, and are bonded together by chemicals, heat and pressure, or needlepunching to give the fabric the desired performance properties.

Melt blown fabric is also a "nonwoven" fabric and is similar to spunbonded fabric in that the resins are extruded. However, the die is different in design and oper-

TABLE I

AVERAGE PROPERTIES OF REEMAY ™ SPUNBONDED POLYESTER

| Fiber Type | Style | Unit Weight oz/yd$^2$ | Thickness mils | Sheet Grab Tensile MD lbs | Sheet Grab Tensile XD lbs | Trapezoid Tear MD lbs | Trapezoid Tear XD lbs | Mullen Burst psi | Frazier Air Perm CFM/ft$^2$ @ 0.5" H$_2$O |
|---|---|---|---|---|---|---|---|---|---|
| | 2006 | 0.6 | 6 | 10 | 8 | 4 | 5 | 11 | 1000 |
| | 2011 | 0.75 | 7 | 14 | 11 | 5 | 6 | 12 | 1050 |
| 4 dpf | 2014 | 1.0 | 8 | 21 | 17 | 7 | 8 | 17 | 800 |
| straight | 2016 | 1.35 | 9 | 29 | 24 | 11 | 12 | 36 | 525 |
| fibers | 2024 | 2.1 | 12 | 50 | 40 | 10 | 11 | 48 | 350 |
| | 2033 | 2.95 | 15 | 83 | 66 | 16 | 19 | 84 | 250 |
| | 2250 | 0.5 | 4 | 10 | 9 | 4 | 4 | 7 | 1100 |
| | 2275 | 0.75 | 6 | 16 | 12 | 5 | 5 | 10 | 875 |
| 2.2 dpf | 2200 | 1.0 | 7 | 21 | 19 | 7 | 8 | 15 | 650 |
| straight | 2214 | 1.35 | 9 | 33 | 34 | 11 | 11 | 34 | 525 |
| fibers | 2295 | 2.95 | 18 | 73 | 70 | 16 | 17 | 76 | 300 |
| | 2410 | 1.15 | 11 | 14 | 11 | 6 | 6 | 9 | 975 |
| | 2415 | 1.55 | 14 | 22 | 16 | 11 | 9 | 16 | 700 |
| 4 dpf | 2420 | 1.85 | 15 | 28 | 22 | 13 | 11 | 18 | 650 |
| crimped | 2430 | 2.4 | 17 | 39 | 32 | 17 | 14 | 29 | 425 |
| fibers | 2440 | 2.9 | 18 | 51 | 45 | 19 | 16 | 38 | 350 |
| | 2470 | 6.0 | 28 | 110 | 100 | 32 | 27 | 82 | 150 | ating principle. As the resin comes from the die, high speed air bursts the resin into fibrils or fibers and directs the fibers to a take-up apron.

The manufacturing process utilizing either a spunbonded fabric or a melt blow fabric includes the following steps:

A. The material, which comes on rolls, is placed on a spindle.
B. The material is fed, on a conveyor, through an oven where it is heated.
C. The heated material is moved, by conveyor, to the next operation where it is formed, under pressure, to its desired configuration.
D. The material is then moved, by conveyor, to the next operation where the formed material is die cut into finished parts.
E. The finished parts are then packaged.
F. The packaged material is then sterilized.

While the present invention has been described in detail and with reference to specific examples thereof, it will be apparent to one skilled in the art that various changes and modifications can be made therein without departing from the spirit and scope thereof. For example, the device of the present invention may be modified for use with general anesthesia gas delivery apparatus, emergency medical gas delivery apparatus or any other apparatus for delivering inhalation gases to successive patients.

What is claimed is:

1. Gas inhalation apparatus comprising:

gas hood for receiving an inhalation gas to be inhaled by a patient, said gas hood means having a cavity into which the inhalation gas may be flowed, said cavity having a gas outlet opening bounded by a peripheral edge portion adapted to circumscribe a face portion of the patient, said gas hood means further having a rear interior side surface portion extending inwardly from said peripheral edge portion; and inhalation gas permeable, essentially shape retaining filter means for filtering inhalation gas being delivered to the patient through said cavity of said gas hood means, said filter means including a unitary hollow body portion removably inserted into said cavity through said gas outlet opening for isolating said face portion from said gas hood means, said hollow body portion having a rear end opening circumscribed by a flange portion configured to overlie and releasably engage said peripheral edge portion and to be pressed betweeen said face portion and said peripheral edge portion in a manner preventing contact between said face portion and said peripheral edge portion, said hollow body portion further having a rear external side surface portion positioned adjacent said flange portion and configured to frictionally engage said rear interior side surface of said gas hood means, to releasably hole said hollow body portion in place within said cavity, whereby said filter means may be rapidly and completely installed on said gas hood means simply by pushing said hollow body portion forwardly into said cavity, removed by pulling said hollow body portion out of said cavity and replaced to ready said gas hood means for use on a subsequent patient by pushing the hollow body portion of an essentially identical filter means into said cavity to bring the flange portion of the replacement body portion, into overlying, releasable engagement with said peripheral edge portion of said gas hood means.

* * * * *

UNITED STATES PATENT AND TRADEMARK OFFICE
CERTIFICATE OF CORRECTION

PATENT NO. : 4,846,170

DATED : July 11, 1989

INVENTOR(S) : Bill H. McAnalley and Wiley F. Walker

It is certified that error appears in the above-identified patent and that said Letters Patent is hereby corrected as shown below:

Column 8, line 23 -- delete "hole" and insert -- hold --.

Signed and Sealed this

Twelfth Day of June, 1990

Attest:

HARRY F. MANBECK, JR.

Attesting Officer

Commissioner of Patents and Trademarks